(12) United States Patent
Moore et al.

(10) Patent No.: US 10,107,740 B2
(45) Date of Patent: Oct. 23, 2018

(54) CUVETTE

(71) Applicant: Analytik Jena AG, Jena (DE)

(72) Inventors: Thomas Moore, Jena (DE); Claus Knippschild, Jena (DE); Martin Hentschel, Jena (DE)

(73) Assignee: Analytik Jena AG, Jena (DE)

( * ) Notice: Subject to any disclaimer, the term of this patent is extended or adjusted under 35 U.S.C. 154(b) by 0 days.

(21) Appl. No.: 15/388,993

(22) Filed: Dec. 22, 2016

(65) Prior Publication Data

US 2017/0184489 A1    Jun. 29, 2017

(30) Foreign Application Priority Data

Dec. 23, 2015   (DE) .......................... 10 2015 122 719

(51) Int. Cl.
*G01N 1/10* (2006.01)
*G01N 21/03* (2006.01)

(52) U.S. Cl.
CPC . *G01N 21/0303* (2013.01); *G01N 2021/0378* (2013.01)

(58) Field of Classification Search
CPC ...... G01N 30/74; G01N 21/031; G01N 21/05; G01N 21/03; G01N 21/0303
USPC ....................................................... 356/246
See application file for complete search history.

(56) References Cited

U.S. PATENT DOCUMENTS

| 6,249,345 | B1 | 6/2001 | Kraack et al. | |
| 2011/0164245 | A1* | 7/2011 | Eikelmann | B01L 3/5088 |
| | | | | 356/246 |
| 2011/0170094 | A1 | 7/2011 | Harnack et al. | |
| 2011/0292383 | A1* | 12/2011 | Gotschy | B01L 3/5085 |
| | | | | 356/246 |
| 2014/0158911 | A1 | 6/2014 | Sahiri et al. | |
| 2014/0340674 | A1* | 11/2014 | Harnack | B01L 3/5088 |
| | | | | 356/246 |
| 2015/0089751 | A1* | 4/2015 | Landa | B65D 1/0223 |
| | | | | 8/406 |
| 2016/0103061 | A1 | 4/2016 | Weber | |

FOREIGN PATENT DOCUMENTS

| DE | 4308202 | A1 * | 9/1994 | ............ G01J 3/0216 |
| DE | 198 26 470 | A1 | 12/1999 | |
| DE | 103 51 160 | B3 | 3/2005 | |

(Continued)

*Primary Examiner* — Md M Rahman
(74) *Attorney, Agent, or Firm* — Duane Morris LLP

(57) ABSTRACT

Cuvette, comprising a first flat plate (1) and a second flat plate (2), both of which in a closed state of the cuvette are positioned so as to be situated opposite parallel to each other and at which there is at least one transparent first measuring surface (1.1) and at least one transparent second measuring surface (2.1), which define in pairs a measuring space (3), in which a liquid sample solution having a drop volume can be held by means of its surface tension and capillary forces. At least the second measuring surface (2.1) of each one of the measuring spaces (3) is a stepped surface, which has at least two plane-parallel partial measuring surfaces (2.1.1, 2.1.2), which are connected to each other by means of a setting surface (2.1.0), so that the partial measuring surfaces (2.1.1, 2.1.2) exhibit different vertical distances ($b_1$, $b_2$) from the first measuring surface (1.1).

8 Claims, 2 Drawing Sheets

(56) References Cited

FOREIGN PATENT DOCUMENTS

| | | |
|---|---|---|
| DE | 10 2007 019 695 A1 | 10/2008 |
| DE | 20 2009 018 896 U1 | 6/2014 |
| DE | 10 2014 113 163 B3 | 12/2015 |
| WO | WO 01/14855 A1 | 3/2001 |
| WO | WO 2012/123395 A1 | 9/2012 |

* cited by examiner

CUVETTE

RELATED APPLICATIONS

The present application claims priority benefit of German Application No. DE 10 2015 122 719.3 filed on Dec. 23, 2015, the contents of each are incorporated by reference in their entirety.

FIELD OF THE INVENTION

The invention relates to a cuvette for tensioning liquid sample solutions, just as it is used for optical measurements in biotechnology or molecular biology and is known, conforming to its genre, from the German patent DE 20 2009 018 896 U1.

BACKGROUND OF THE INVENTION

Optical measuring of sample solutions is part of the standard procedures in, in particular, biotechnology or molecular biology. The analysis of the interactions between electromagnetic radiation and molecules or atoms in sample solutions, such as, for example, the transmission, reflection, absorption, fluorescence or scattering, allows a number of conclusions to be drawn about the compositions of the samples or the course of the biochemical processes.

In particular, the determination of a molar sample concentration of the sample solution is often performed in bioanalysis by measuring the extinction of monochromatic light of specific wavelengths. Under certain conditions the Lambert-Beer law, with which an unknown concentration can be determined either directly or by means of a calibration curve, applies here. In addition to the monochromatic light and constant external conditions, the presence of an ideal sample solution is a requirement for the application of the Lambert-Beer law. Only in the case of ideal sample solutions does the sample solution show the requisite linear dependency between the extinction and the concentration of the sample. Ideal sample solutions are concentrated so negligibly that between the dissolved molecules there cannot occur any interactions that could lead to non-linear dependencies. Under these conditions the measured extinction is proportional to the concentration and optical wavelength through the sample solution (layer thickness). An ideal sample solution can be produced by, for example, reducing too high a concentration of the sample by dilution. The range of the linear dependency can also be achieved by decreasing the layer thickness (for example, by using a flatter sample vessel) of a too highly concentrated sample until interactions can no longer occur.

Usually the layer thickness is determined by measuring a sample vessel, with which the sample solution is fed into the measuring device.

Sample vessels that are widely used include cuvettes, in which the sample solution is received in a measuring chamber between two optically transparent side walls. Such cuvettes are typically standardized, so that their receiving volume can be assigned a distance from the two optically transparent side walls and, as a result, a layer thickness of the measuring chamber. One drawback with such cuvettes is that the standardized volume content of >50 µl is usually too large for the very small sample amounts of <10 µl, which are customary in biotechnology or molecular biology. In addition, the volume content is fixed, so that it is not possible to change the layer thickness. Especially in the case of cuvettes that are intended for small sample volumes and have narrow and deep-lying measuring chambers, cleaning is barely possible. For this reason these cuvettes are usually designed as disposable articles and are not reusable.

The prior art also discloses reusable cuvettes for smaller sample amounts. The cuvettes, which are disclosed in the Offenlegungsschrift [published patent application] WO 2012/123395 A1 by the company HELLA GmbH and which are marketed under the name "TrayCell", are suitable for sample volumes ranging from 0.7 to 10 µm. Compared to standard cuvettes, these cuvettes are very time-consuming to produce and, as a result, expensive.

Even in the case of cuvettes having different layer thicknesses the prior art has solutions. The Offenlegungsschrift DE 198 26 470 A1 discloses a cuvette, which is made of a synthetic plastic material and which comprises a measuring chamber having a rectangular cross section at a side ratio of preferably 5:1. The four side walls of the measuring chamber are optically transparent, so that the cuvette, rotated by 90 deg., can also be received in the measuring device. Owing to the rectangular cross section of the measuring chamber the sample can be easily measured in two layer thicknesses. The drawback is the large volume of the measuring chamber of ≥50 µl. The cuvette is made of a synthetic plastic material. Due to the lesser transparency for UV rays said cuvette does not lend itself very well to measurements with wavelengths of 220 nm. In addition, the cuvette is designed as a disposable article and cannot be reused again.

Another concept, in which small volumes of sample solutions can be measured in different layer thicknesses, is known from the German patent DE 10 2007 019 695 A1. In this case the invention relates to a chip cuvette in the form of a flat, planar support substrate, into which one or more measuring chambers and a channel system, connecting the measuring chambers, for receiving a sample volume are introduced. The channels and the measuring chambers are sealed with an optically transparent film. The measuring chambers of a chip cuvette can be configured so as to have different depths, so that a sample can be measured in different layer thicknesses. The chip cuvette is designed as a disposable article and cannot be reused.

In the aforementioned cuvettes the layer thickness of the sample solution is determined by the dimensioning of a measuring chamber, which is formed by a bottom and side walls and into which the sample liquid is filled. The measuring chamber forms the measuring volume respectively.

Another concept for a cuvette is known from the German patent DD 1077 83 B1. The described cuvette (called sample holder in this case) consists of two, essentially flat, transparent plates, which have surface structures on their surfaces that face each other; and their surface structures define the measuring surfaces (sample bearing regions in said patent). The two plates are arranged at a defined distance from each other, so that the measuring volumes, formed between the measuring surfaces, are limited laterally only by air. With respect to the measuring surfaces, they are designed in such a way that they are advantageously in the same plane as the other regions of the plate and are separated from said regions by ring-shaped grooves.

The plates are designed in such a way that they can be moved towards each other and have mechanical means for fixing their position with respect to each other. The cuvette is provided for extremely small measuring volumes of a few µl.

Even in the case of a device known from the Offenlegungsschrift WO 01/14855 A1, a small measuring volume of the sample solution of ≤10 µl in drop form is tensioned between two parallel optical surfaces, which are situated opposite each other, and is held in said drop form only by the surface tension of the liquid. In order to change the layer thickness of the sample solution, the distance between the optical surfaces can be varied in three positions by means of a controllable spacer, where in this case the drop can be compressed or pulled apart in accordance with the surface tension. Each of the opposing optical surfaces is formed as a raised surface on a leg, where in this case the two legs are connected to each other by means of a hinge at one of their two ends. The device can be folded open, so that the optical surfaces are freely accessible to receive the sample and are easy to clean. This feature makes the device reusable. This solution to the problem assumes greater complexity for driving and controlling the optical surfaces that can be moved towards each other. In addition, the different layer thicknesses can only be measured one after the other in succession, since the distance between the optical surfaces has to be changed between the measurements.

The aforementioned DE 20 2009 018 896 U1 discloses a cuvette comprising at least one measuring surface on each of the two legs (there arms), which are connected to each other by means of a swivel joint. When the cuvette is folded together, the legs are folded into a measuring position, in which the two measuring surfaces are situated opposite parallel to each other at a distance. The distance is suitable for holding a liquid sample between the measuring surfaces. In the closed state such a cuvette can be inserted into an optical measuring device in such a way that it crosses the light beam path of the measuring device; and the liquid sample is positioned in the light beam path. This patent discusses a wide variety of embodiments of a cuvette, in which the material and the geometry of the cuvette or also the surface of the measuring surfaces are varied. In each case, however, the measuring surface is a flat surface, so that the measuring surfaces are at the same distance from each other over the whole measuring range defined by said measuring surfaces. The distance between the two measuring surfaces can be set with a high degree of accuracy during the production of the cuvette, so that the cuvette is designed specifically for a thickness of the sample that is the result of the set distance. The cuvette may have one measuring range, but also a plurality of measuring ranges defined by two measuring surfaces.

The cuvettes (measuring plate cuvettes), disclosed in the aforementioned documents DD 1077 83 B1, WO 01/14855 A1 and DE 20 2009 018 896 U1, have in common that the liquid sample is held statically as a drop (drop volume) between two measuring surfaces by interfacial tension and adhesive force. The interfacial tensions denote the forces that act on the boundary between two different phases that are in contact with each other. That means that the two phases form a common interface that is under interfacial tension. In the case of the cuvettes disclosed in the aforementioned documents, there are in each case two interfaces between the drop and a glass surface and one interface between the drop and a gas, for example, air. The interfacial tension between a liquid and a gas is also referred to as the surface tension. A volume of a liquid, which is held together solely by the interfacial tension and adhesive force between the interfaces, constitutes a drop volume. A drop volume is in the range of 0.1 to 10 µl. Depending on the properties of the liquid and the surface finish of the measuring surfaces, the distance between the two measuring surfaces is limited to a range of 100 mm to 1.0 mm, so that a drop volume can be held between the two measuring surfaces.

In contrast to the aforesaid, larger volumes, which fill statically or dynamically a cuvette in the form of a container, for example, a box (box cuvette), follow the internal shape of the cuvette, for which reason there is no limit to be observed in the upward direction for dimensioning the distance between the measuring surfaces.

SUMMARY OF THE INVENTION

An object of the present invention is to find a cuvette that is simpler in design and with which the measurement of a sample solution in the drop volume in different layer thicknesses is possible.

This object is achieved, according to the invention, by means of a cuvette comprising a first flat plate having a first inner surface and a second flat plate having a second inner surface. In a closed state of the cuvette the first and second inner surfaces are positioned in such a way that they are situated opposite parallel to each other at a vertical distance. Inside the first inner surface there is at least one transparent first measuring surface; and inside the second inner surface there is at least one transparent second measuring surface. They define in pairs a measuring space, in which a liquid sample solution can be held by means of its interfacial tension and capillary forces. At least the second measuring surface of each one of the measuring spaces is a stepped surface. It has at least two plane-parallel partial measuring surfaces, which are connected to each other by means of a setting surface, so that the partial measuring surfaces exhibit different vertical distances from the first measuring surface.

At least one of the measuring surfaces, defining the at least one measuring space, is formed advantageously on an optical element, which is inserted into the first or second flat plate.

This feature is especially advantageous in terms of production, if the at least two partial measuring surfaces are raised with respect to the second inner surface, so that the distance between the first and the second inner surfaces is greater than the first distance between the first partial measuring surface and the first measuring surface and the second distance between the second partial measuring surface and the first measuring surface.

Especially if the partial measuring surfaces are to be brought into a light beam path of a measuring device at the same time, it is advantageous if the second measuring surface of a respective measuring space is circular; and the partial measuring surfaces constitute sectors of a circle.

If the partial measuring surfaces are to be brought into a light beam path of a measuring device one after the other in succession, it is advantageous if the second measuring surface of a respective measuring space is rectangular; and the partial measuring surfaces constitute rectangles.

In order for the radiation, transmitting exclusively through the partial measuring surfaces, to contribute to the measurement results, the setting surface has a reflective coating.

At least one of the two measuring surfaces, which form a measuring space, can also be enclosed by a groove, a feature that is advantageous in terms of production, if the measuring surfaces are formed directly on the inner surfaces of the flat plates.

BRIEF DESCRIPTION OF THE DRAWINGS

The invention will be explained in greater detail below by means of exemplary embodiments. The associated drawings show in.

DETAILED DESCRIPTION OF THE DRAWINGS

Figure 1:
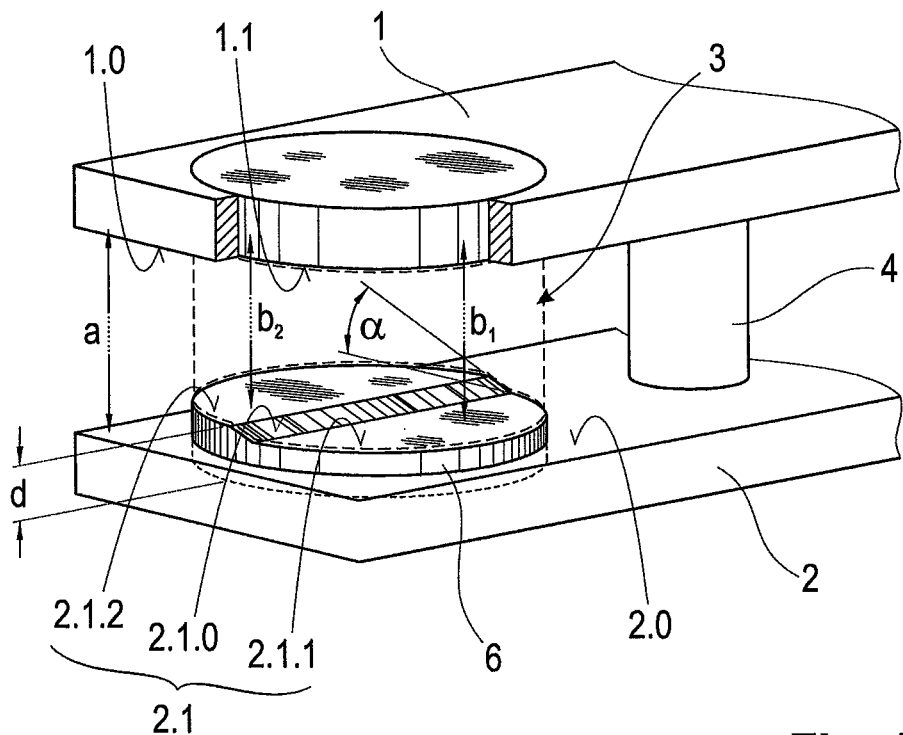
FIG. 1 is the basic design of a cuvette with a specific representation of a first embodiment of the measuring space.

Basically the cuvette is constructed, as shown in FIG. 1. Said cuvette consists of a first flat plate 1 having a first inner surface 1.0 and a second flat plate 2 having a second inner surface 2.0. In a closed state of the cuvette the first and second inner surfaces 1.0, 2.0 are positioned in such a way that they are situated opposite and parallel to each other at a vertical distance a. Inside the first inner surface 1.0 there is at least one transparent first measuring surface 1.1; and inside the second inner surface 2.0 there is at least one transparent second measuring surface 2.1. The first and second measuring surfaces 1.1, 2.1 define in pairs a measuring space 3, in which a liquid sample solution having a drop volume can be held by means of adhesive forces and its surface tension. In contrast to the prior art, the second measuring surface 2.1 of a respective measuring space 3 represents a stepped surface, which is formed by means of at least two plane-parallel partial measuring surfaces 2.1.1, 2.1.2, which are connected to each other by means of a setting surface 2.1.0 and which form in each case a partial measuring space with a vertically opposing cut-out of the first measuring surface 1.1. The at least two partial measuring surfaces 2.1.1, 2.1.2 are at different vertical distances $b_1$, $b_2$ from the first measuring surface 1.1.

Each of the two distances b1 and b2 has to be greater than a specified minimum distance and less than a specified maximum distance, so that the drop volume can remain stable in both partial measuring spaces. The result is a maximum allowable difference in the distance that all of the partial measuring surfaces 2.1.1, 2.1.2 may have with respect to each other. Depending on the properties of the liquid and the surface finish of the measuring surfaces 1.1, 1.2, the specified minimum distance and the specified maximum distance are in a range of 100 mm to 1.0 mm.

In principle, the first measuring surface 1.1 can also represent the same stepped surface as the measuring surface 2.1, a feature that, however, does not offer any obvious advantage, for which reason this possibility is not taken into consideration below.

As shown in FIG. 1, the distances $b_1$ and $b_2$ are preferably less than the distance a, so that the liquid sample solution is held between the measuring surfaces 1.1, 2.1 by capillary forces.

Figure 2:
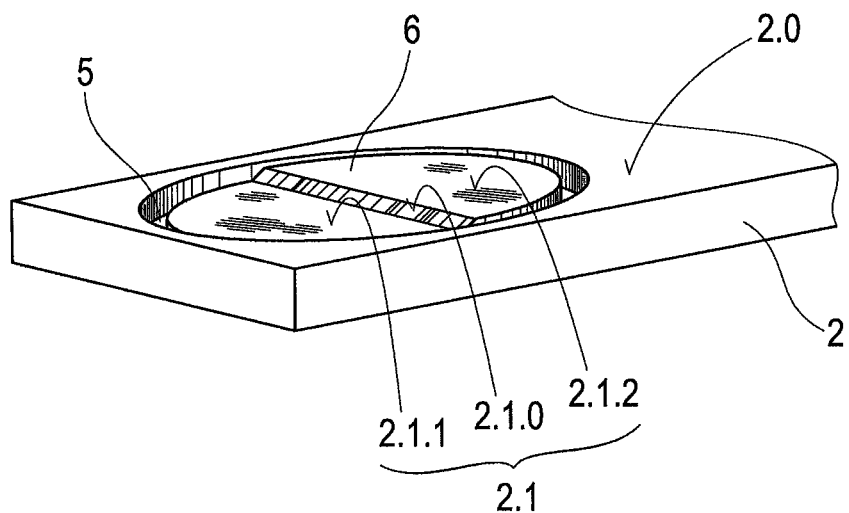
FIG. 2 is a partial view of the measuring space in a second embodiment.

However, the distances $b_1$ and $b_2$ can also be greater than or one can be equal to the distance a, if, as shown in FIG. 2, a closed groove 5 is formed around at least one of the two measuring surfaces 1.1, 2.1, as a result of which the inner surfaces 1.0, 2.0 in the region of the groove 5 exhibit a distance that is greater than the distance a and the distances $b_1$ and $b_2$.

In principle, the measuring surfaces 1.1, 2.1 may have any circumferential shape. In practice, however, they are designed rectangular, as in FIGS. 3c and 3d; they are designed round, as shown in FIGS. 1, 2, 3a and 3b, or oval. Rectangular or oval is advantageous, if a measuring radiation is applied to the partial measuring spaces in succession, whereas round is the best shape, if a measuring radiation is supposed to pass through both partial measuring spaces at the same time.

In the event that the cuvette has a plurality of partial measuring spaces, they are arranged advantageously in a row (not shown). In this case all of the distances bn of the n partial measuring surfaces 2.1.1, 2.1.2 have to be greater than the specified minimum distance and smaller than the specified maximum distance. That is, in total they may not exceed the maximum allowable difference in distance.

The measuring surfaces 1.1, 2.1 may be machined monolithically out of the flat plates 1, 2, if said flat plates are made of an optically transparent material or may be formed on optically transparent elements, which are inserted into the flat plates 1, 2. The measuring surfaces 1.1, 2.1 of a measuring space 3 have an identical peripheral shape.

The setting surface 2.1.0 between two adjacent partial measuring surfaces 2.1.1, 2.1.2 encloses with these partial measuring surfaces an angle α that is greater than 5 deg. and less than 35 deg. In the case of a very suitable difference in the distances b1, b2 with respect to each other, less than 5 deg. would result in an unnecessarily wide setting surface 2.1.0; and greater than 35 deg. would result in the bursting of the drop, formed by the drop volume. The setting surface 2.1.0 causes the drop volume to split and flow over between the partial measuring surfaces 2.1.1, 2.1.2 from the smaller to the larger distance to be measured. The setting surface may be hydrophobically coated, so that the drop will split. Then the entire drop volume will be distributed among the partial measuring spaces and can be used for measurements. The angle α may be chosen in such a way that the width of the setting surface 2.1.0 may be determined as a function of the difference in the distance between the adjacent partial measuring surfaces 2.1.1, 2.1.2, as a result of which the distance between the partial measuring regions 2.1.1, 2.1.2 can be adapted to the external measurement conditions.

The specific size of the drop volume, on the one hand, and the dimensioning of the setting surface 2.1.0 and the partial measuring surfaces 2.1.1, 2.1.2, as well as their distances b1, b2 and, as a result, their distance ratio, on the other hand, are interdependent. A phase of less than 0.1 mm×45 deg. is designed advantageously at the transition between the setting surface 2.1.0 and a partial measuring surface 2.1.1, 2.1.2.

In FIG. 1 a first embodiment of a measuring space 3 is not shown true to scale. The first measuring surface 1.1, which is formed on the first inner surface 1.0 of the first flat plate 1, and the second measuring surface 2.1, which is formed on the second inner surface 2.0 of the second flat plate 2, are designed circular. The second measuring surface 2.1, which is formed, according to the invention, by means of a stepped surface, is divided in the middle, so that the first partial measuring surface 2.1.1 and the second partial measuring surface 2.1.2 are semicircular sectors of a circle, if the surface requirement of the setting surface 2.1.0 is disregarded. The first measuring surface 1.1 is flat and at least as large or larger than the second measuring surface 2.1. The vertical first distance $b_1$ between the first partial measuring surface 2.1.1 and the first measuring surface 1.1 is greater than the vertical second distance $b_2$ between the second partial measuring surface 2.1.2 and the first measuring surface 1.1. In order for the flat plates 1, 2 to exhibit the distance a with respect to each other in the working state, the cuvette has suitable means that were previously known from the prior art and that are described herein after the description of the exemplary embodiments of the measuring space 3.

In order to make sure that the second measuring surface 2.1 can be seen in FIG. 1, the distances a, $b_1$ and $b_2$ are shown in a highly exaggerated fashion. Under actual conditions the second measuring surface 2.1 would be covered by the first flat plate 1 when the first and second measuring surfaces 1.1 and 2.1 are situated opposite and parallel to each other.

The liquid sample solution is received in the measuring space 3, formed between the pair of first and second measuring surfaces 1.1 and 2.1. The liquid sample solution is held by means of its surface tension and the capillary action between the parallel measuring surfaces 1.1 and 2.1. In order to limit the distribution of the liquid sample solution to the measuring space 3, the distance between the measuring surfaces 1.1, 1.2 has to be less than the distance between the directly adjacent surfaces that are the inner surfaces 1.0, 2.0 or the bottom surface of at least one groove 5, formed in one of the inner surfaces 1.0, 2.0. Due to the small first and second distances $b_1$ and $b_2$, a small measuring space 3 is formed that requires correspondingly only a small volume of the liquid sample solution of x-y µl. The liquid sample solution that is injected into the cuvette fills advantageously the entire measuring space 3. Otherwise the capillary forces, which are stronger in the region of the second partial measuring surface 2.1.2 due to the smaller second distance $b_2$, would partially drain the volume in the region of the first partial measuring surface 2.1.1. In order to ensure that this situation does not have an effect on the measurement that is carried out with the cuvette, the partial measuring spaces are dimensioned in such a way that when the partial measuring space is not completely filled, the measurement radiation is passed through the volume of the liquid sample solution.

The preferably symmetrical division of the second measuring surface 2.1 into the first partial measuring surface 2.1.1 and the second partial measuring surface 2.1.2 is carried out at the flat setting surface 2.1.0. Then the setting surface 2.1.0 is arranged along the diameter of the second measuring surface 2.1. The setting surface 2.1.0 allows a difference in the first distance $b_1$ and the second distance $b_2$ to be bridged between the partial measuring surfaces 2.1.1 and 2.1.2. The setting surface 2.1.0 is arranged at an angle α of 35 deg.≥α≥5 deg. to the parallel partial measuring surfaces 2.1.1 and 2.1.2. The setting surface 2.1.0 can be coated, so that no radiation can penetrate through said setting surface and that the measurement result is caused exclusively by the liquid sample solution in the partial measuring spaces.

In comparison to the embodiment that is shown in FIG. 1 and that is produced preferably by inserting an optical element 6, on which the second measuring surface 2.1 is formed, into the second flat plate 2, in FIG. 2 a closed groove 5 is formed around the second measuring surface 2.1; and the second measuring surface 2.1 is machined out of the second flat surface 2. The distance $b_1$ is advantageously greater than the distance a; and the distance $b_2$, which is always less than the distance $b_1$, is equal to or also greater than the distance a. However, it may be difficult to machined, for example, polish, the two partial measuring surfaces 2.1.1, 2.1.2, which are then set deeper with respect to the second inner surface 2.0, for which reason it may also be practical to design both partial measuring surfaces 2.1.1, 2.1.2 in such a way that they are elevated with respect to the second inner surface 2.0 by removing the second inner surface 2.0 around the second measuring surface 2.1. Then it is possible to dispense with the groove 5, as shown in FIG. 1.

Figure 3A:
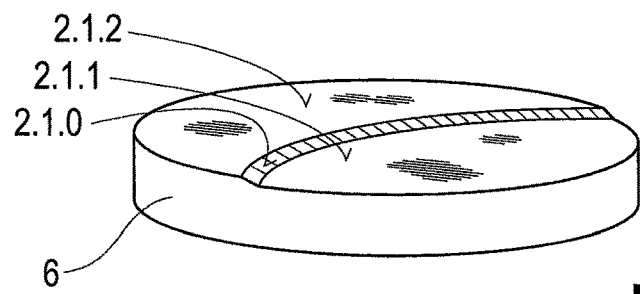
FIGS. 3a to 3d are views of the second measuring surface in different embodiments.
Figure 3B:
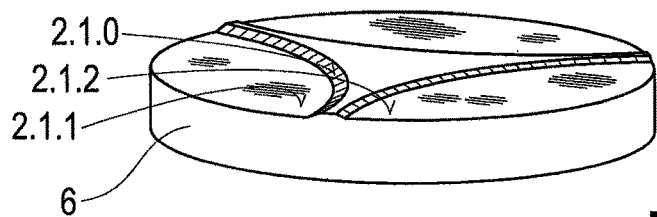

Since the setting surface 2.1.0 has no optical function, but rather is only supposed to connect in a surface to surface manner the partial measuring surfaces 2.1.1, 2.1.2, said setting surface can have any surface shape. In practice, however, it is designed flat, as shown in FIGS. 1 and 2, or continuously curved, as shown in FIGS. 3*a* and 3*b*.

The division of the second measuring surface 2.1 by means of flat or curved setting surfaces 2.1.0 can also be effected in more than two partial measuring surfaces 2.1.1, 2.1.2, with other geometric shapes of the partial measuring surfaces 2.1.1, 2.1.2 and in any desired relative size, as long as the division is necessary for filling a measuring task.

Figure 3C:
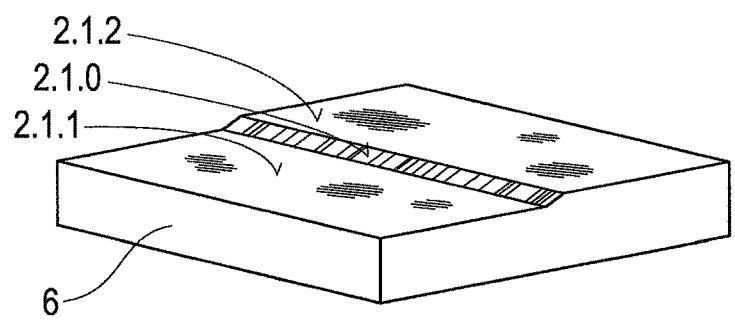
Figure 3D:
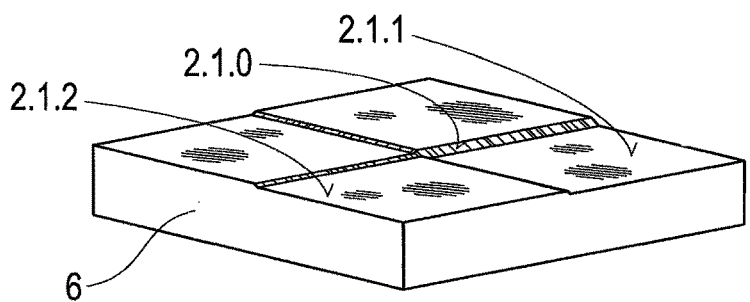

The measuring surfaces 3, shown in FIGS. 3*c* and 3*d*, are different from those described above due to their outer contour. In this case the first measuring surface 1.1, which is formed on the first inner surface 1.0 of the first flat plate 1, and the second measuring surface 2.1, which is formed on the second inner surface 2.0 of the second flat plate 2, are designed rectangular. The setting surface 2.1.0 extends linearly and parallel to the boundary of the measuring surfaces 1.1 and 2.1, so that the first and second partial measuring surfaces 2.1.1 and 2.1.2 are also rectangular.

The embodiments of a cuvette are not limited to the examples that are actually shown and described. The outer contours of the measuring surfaces 3, the relative positions of the partial measuring surfaces 2.1.1, 2.1.2 of the second measuring surface 2.1 to the second inner surface 2.0, the relative position of the first measuring surface 1.1 to the first inner surface 1.0, with and without the groove 5 around the measuring surfaces 1.1, 2.1, the embodiment of the setting surfaces 2.1.0, as well as the number of partial measuring surfaces 2.1.1, 2.1.2 and their geometric division can be combined with each other. That is, other advantageous embodiments of the cuvette may be formed by a combination of the aforementioned features of different geometric shapes of the measuring surfaces and different kinds and arrangements of the setting surfaces 2.1.0. Of course, other geometric shapes of the measuring surfaces 1.1 and 2.1, such as, for example, ellipses, rings, triangles, etc. can also be used. In the case of more than two partial measuring surfaces 2.1.1, 2.1.2, it is also possible that the setting surfaces 2.1.0 intersect or extend, starting from the edge of the second measuring surface 2.1, from one common starting point to the second measuring surface 2.1.

All of the exemplary embodiments have in common the basic design of the cuvette of the previously known prior art. In order to measure a liquid sample solution in the light beam path of a measuring device, the cuvette provides a drop volume of the liquid sample solution, through which the measuring radiation passes over a defined optical path length. This optical path length is determined in the same way as in the case of all of the cuvettes of the prior art by means of the wall thickness and the distance between two opposite walls of the cuvette.

The cuvette walls are formed, according to the invention, by the first and second flat plates 1, 2. Correspondingly in this case the wall thickness of the cuvette wall is the thickness d of the flat plates 1, 2 in the region of the measuring surfaces 1.1, 2.1 or, more specifically, the inserted optical element 6, as mentioned by way of example in FIG. 1.

The closed state of the cuvette is produced by positioning the two flat plates 1, 2 at a vertical distance from each other and by fixing them temporarily in this state.

In addition, the flat plates 1, 2, which are positioned with respect to each other, can be inserted, for example, in a conventional cuvette, formed by a measuring space 3, or can be received by a holding device.

The flat plates 1, 2 can also be connected to each other on one side by mechanical means. This mechanical connection allows such a cuvette, which is often referred to as a Klapp cuvette, to be brought into two states. In a closed state, also working state, the flat plates 1, 2 are arranged with their inner surfaces 1.0, 2.0 at a distance a from each other; and the liquid sample solution can be held in the existing measuring spaces 3. In an open state, also cleaning or filling state, the measuring surfaces 1.1, 2.1 are easily accessible in order to clean them or to apply a liquid sample solution. The distance a can be defined by an end position of the mechanical connection. That is, the flat plates 1, 2, defined by the range of motion of the mechanical connection, can be set one above the other no further than to the distance a. However, it is simpler if in order to maintain the distance a there is a stop on at least one of the two flat plates 1, 2. This stop can be, for example, a frame, frame elements or spacers 4 that are present between the measuring surfaces 1.1, 2.1.

In order to carry out the mechanical connection, there are a wide variety of solutions. Relevant is that in the folded together state the inner surfaces 1.0, 2.0 are arranged parallel to each other and at a distance a from each other. The simplest connection is a monolithic joint between the flat plates 1, 2, comparable to tweezers. Another known option is the use of a hinge, where the two flat plates 1 and 2 are connected to each other by means of an axis of rotation. It is also known to connect the flat plates 1, 2 by means of swivel arms, which are arranged in the shape of a parallelogram; and these swivel arms are arranged on both sides of the flat plates 1, 2.

As stated above, the first and second measuring surfaces 1.1 and 2.1 can be attached advantageously to the end face of a respective cylindrical optical element 6. Each of the optical elements 6 is received and fastened to the inner surfaces 1.0 or 2.0 of one of the flat plates 1, 2 in a through-bore, where in this case the through-bores represent the passage opening for the light beam path of the measuring device. The receiving is effected in such a way that the measuring surfaces 1.1 and 2.1 are situated opposite each other and are elevated with respect to the inner surfaces 1.0 and 2.0. The elevation ensures that the distance a between the inner surfaces 1.0 and 2.0 is always much greater than the distances $b_1$ and $b_2$ between the measuring surfaces 1.1 and 2.1 and that the liquid sample solution, which is held by the capillary action and the surface tension between the measuring surfaces 1.1 and 2.1, cannot escape from the measuring volume. Another advantage of forming the measuring surfaces 1.1, 2.1 on the inserted optical elements 6 is that these optical elements can be made independently of the rest of the cuvette with high precision and surface finish and do not have to be mounted in the cuvette until afterwards. Then the flat plates 1, 2 can be made of any stable material and do not themselves have to be transparent.

It is particularly advantageous if the cylindrical optical elements 6 are made of quartz glass and are produced by the sol-gel process. Compared to transparent plastics, quartz glass has better transmission properties at wavelengths in the UV range. Compared to conventional methods, the sol-gel process offers the advantages of being able to produce inexpensively a basic shape of the optical element 6, bearing the second measuring surface 2.1, with the stepped partial measuring surfaces 2.1.1, 2.1.2.

Since in order to define the measuring space 3 it is already sufficient if only the second measuring surface 2.1 is offset from the second inner surface 2.0, a region of the first inner surface 1.0 of the first flat plate 1 can also be used as the first measuring surface 1.1. To this end the first flat plate 1 is designed transparent and is surface-treated in its entirety or only in the regions of interest, in order to obtain the requisite optical quality.

A different geometric design of the partial measuring surfaces 2.1.1, 2.1.2 and their arrangement with respect to each other make it possible to configure the partial measuring spaces, which are defined thereby, in different geometric shapes and to arrange them with respect to each other. For measurements the individual partial measuring spaces of a respective measuring space 3 can be brought into a light beam path of a measuring device chronologically or also simultaneously.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

LIST OF REFERENCE NUMERALS

1 first flat plate
1.0 first inner surface
2 second flat plate
2.0 second inner surface
1.1 first measuring surface
2.1 second measuring surface
2.1.0 setting surface
2.1.1 first partial measuring surface
2.1.2 second partial measuring surface
3 measuring space
4 spacer
5 groove
6 optical element
α angle
d thickness
a vertical distance between the first and the second inner surfaces 1.0, 2.0
$b_1$ vertical first distance between the first partial measuring surface 2.1.1 and the first measuring surface 1.1
$b_2$ vertical second distance between the second partial measuring surface 2.1.2 and the first measuring surface 1.1

What is claimed is:

1. A cuvette, comprising a first flat plate having a first inner surface and a second flat plate having a second inner surface, wherein in a closed state of the cuvette the first and second inner surfaces are positioned so as to be situated opposite and parallel to each other at a first vertical distance; and inside the first inner surface there is at least one transparent first measuring surface and inside the second inner surface there is at least one transparent second measuring surface, both of which define in pairs a measuring space, in which a liquid sample solution having a drop volume can be held by means of its interfacial tension and capillary forces, said at least one second measuring surface of said measuring space is a stepped surface, said stepped surface having at least two plane-parallel partial measuring surfaces which are connected to each other by means of a setting surface, wherein said partial measuring surfaces are spaced from said first measuring surface by second and third vertical distances respectively, said second and third vertical distances being different from each other, and wherein the setting surface encloses with the plane-parallel partial measuring surfaces an angle of between 5 and 35 degrees.

2. The cuvette, as claimed in claim 1, wherein at least one of the measuring surfaces, defining the at least one measuring space, is formed on an optical element, which is inserted into the first or second flat plate.

3. The cuvette, as claimed in claim 2, wherein said at least two partial measuring surfaces are elevated with respect to the second inner surface, so that the first vertical distance is greater than the second vertical distance and the third vertical distance.

4. The cuvette, as claimed in claim 1, wherein said at least two partial measuring surfaces are elevated with respect to the second inner surface, so that the first distance is greater than the second vertical distance and the third vertical distance.

5. The cuvette, as claimed in claim 1, wherein said second measuring surface of a respective measuring space is circular; and said partial measuring surfaces constitute sectors of a circle.

6. The cuvette, as claimed in claim 1, wherein said second measuring surface of a respective measuring space is rectangular; and said partial measuring surfaces constitute rectangles.

7. The cuvette, as claimed in claim 1, wherein said setting surface has a reflective coating.

8. The cuvette, as claimed in claim 1, wherein at least one of the two measuring surfaces of the at least one measuring space is enclosed by a groove.

\* \* \* \* \*